Feb. 13, 1973 V. P. QUINN Plant Pat. 3,305
CARNATION
Filed June 21, 1971
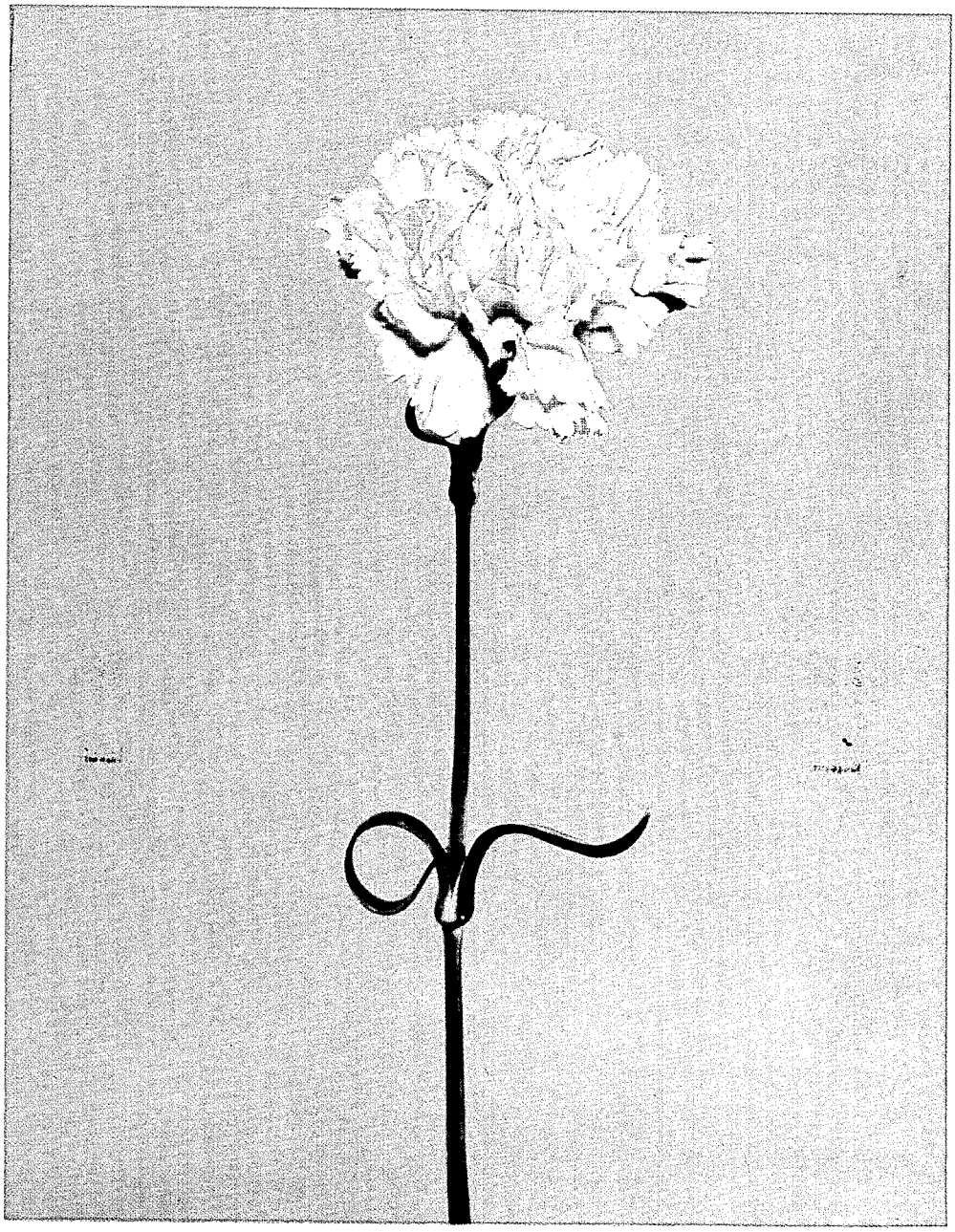
INVENTOR.
Vincent P. Quinn
BY
Van Valkenburgh & Lowe
ATTORNEYS

United States Patent Office

Plant Pat. 3,305
Patented Feb. 13, 1973

3,305
CARNATION

Vincent P. Quinn, 1235 S. Irving St., Denver, Colo. 80219

Filed June 21, 1971, Ser. No. 155,366
Int. Cl. A01h *5/00*
U.S. Cl. Plt.—70 1 Claim

This invention relates to improvements in carnations, and the object of the invention is to provide a new and distinct variety of carnation plant in which the blossom is of a distinctive color and the growth is greatly improved.

This new variety, identified as "Quinn's Orange," is a diploid sport from "Quinn's Yellow" for which applicant has filed an application for U.S. plant patent, Ser. No. 155,365, filed June 21, 1971, which in turn was a sport from the "Tangerine" of Plant Patent No. 1,734. The plant of the present invention has a bloom of a different color than "Quinn's Yellow" and is similar to but slightly different from the color of "Tangerine," but has better growth habits than "Tangerine." Thus, the new variety has more vigorous growth, flowers faster, has stronger stems and has a better root system than carnations of a similar color. The plant of the present invention has been registered as a new and distinct variety of carnation with the American Carnation Society.

Asexual reproduction of this new variety was made at Denver, Colo., by taking cuttings and growing and selecting them in 1968, 1969 and 1970. The cuttings have consistently produced blossoms having the color hereinafter described in more detail.

In comparison tests with the finest selection of "Tangerine" obtainable, in adjacent test plots, the growth rate of the plant of the present invention was faster, the quality was higher, and the longevity was greater, as follows:

| | Quinn's orange | Tangerine |
|---|---|---|
| Number of plants | 7 | 7 |
| Grade: | | |
| Super Fancy | 80 | 0 |
| Fancy | 16 | 6 |
| Commercial | 16 | 77 |
| Number of blooms | 102 | 83 |
| Longevity, days | 7 | 5 |

The accompanying illustration is a color photograph of a flower of this new variety.

Following is a detail description of the flower and plant of this new variety. Plate references are to the Dictionary of Color, Maerz and Paul, Second Edition, McGraw Hill (1950).

*The plant*

Growth: Vigorous and upright. Can withstand vigorous watering.

Flowering habit: Very productive of good blooms. Can be forced for all flowering.

Stems: Very strong and upright. Internodes 3½ to 4 inches long. Nodes: Large. Color: Chrome green, deep but with gray overlay to give bluish green color (Plate 24, row 12, column J).

Foliage:

*Size.*—Average 4 inches long and ⅜ to ½ inch broad.

*Habit.*—Bottom foliage curls, top foliage straight.

*Color.*—Leaves same as stem.

*Quantity.*—Average.

Flower:

*Size.*—Large, averaging about 4 inches in diameter under normal greenhouse culture.

*Color.*—Between melon and coral geranium (Plate 2, row 10, columns D through J). This color does not change during the lifetime of the flower.

*Form.*—Full petaled, high centered and regular, with outer edge almost an unbroken circle.

*Calyx.*—Approximately parrot green (Plate 21, row 6, column K). Very strong, tough and non-splitting.

*Longevity.*—Longer lasting than "Tangerine." Average picking quality.

*Fragrance.*—Mild and pleasant.

*Petals.*—Slightly fringed but not deeply cut. Guard petals are 1 to 1½ inches in width and spread to form a generally circular plane. Other petals are folded and tightly bunched together so that separate petals are not distinguishable.

Reproductive organs:

*Ovary.*—Large; high; pithy.

*Pistils.*—Small; curved but not curled; from ¾ to 1½ inches long; usually divided into two or three branches; seldom long enough to be visible in the open flower.

*Stamens.*—White; few; without anthers.

Having thus disclosed this discovery of a new variety of asexually reproduced plant, I claim:

1. The new and distinct variety of carnation plant, substantially as herein described and illustrated.

No references cited.

ROBERT E. BAGWILL, Primary Examiner